US00PP27410P2

(12) United States Plant Patent
Ludwig

(10) Patent No.: US PP27,410 P2
(45) Date of Patent: Nov. 22, 2016

(54) *PETUNIA* PLANT NAMED 'SUTULIM'

(50) Latin Name: *Petunia×hybrida*
Varietal Denomination: Sutulim

(71) Applicant: Andrea Ludwig, Dresden (DE)

(72) Inventor: Andrea Ludwig, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 162 days.

(21) Appl. No.: 14/121,965

(22) Filed: Nov. 7, 2014

(51) Int. Cl.
*A01H 5/02* (2006.01)

(52) U.S. Cl.
USPC ..... Plt./356.15

(58) Field of Classification Search
USPC ..... Plt./356.15
See application file for complete search history.

*Primary Examiner* — Keith Robinson
(74) *Attorney, Agent, or Firm* — C. A. Whealy

(57) ABSTRACT

A new and distinct cultivar of *Petunia* plant named 'Sutulim', characterized by its upright and mounding plant habit; moderately vigorous growth habit; freely branching habit; early and freely flowering habit; white-colored flowers with yellow green-colored venation and centers; resistance to mildew; and good garden performance.

2 Drawing Sheets

Botanical designation: *Petunia×hybrida.*
Cultivar denomination: 'SUTULIM'.

BACKGROUND OF THE INVENTION

The present invention relates to a new and distinct cultivar of *Petunia* plant, botanically known as *Petunia×hybrida* and hereinafter referred to by the name 'Sutulim'.

The new *Petunia* plant is a product of a planned breeding program conducted by the Inventor in Dresden, Germany. The objective of the breeding program is to create new uniform *Petunia* plants with freely branching and flowering habit, attractive flower coloration and resistance to mildew.

The new *Petunia* plant originated from a cross-pollination made by the Inventor during the summer of 2008 of two unnamed proprietary selections of *Petunia×hybrida*. The new *Petunia* plant was discovered and selected by the Inventor as a single flowering plant within the progeny of the stated cross-pollination in a controlled environment in Dresden, Germany during the summer of 2009.

Asexual reproduction of the new *Petunia* plant by terminal cuttings in a controlled environment in Dresden, Germany since the summer of 2009, has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sutulim'. These characteristics in combination distinguish 'Sutulim' as a new and distinct *Petunia* plant:

1. Upright and mounding plant habit.
2. Moderately vigorous growth habit.

3. Freely branching habit.
4. Early and freely flowering habit.
5. White-colored flowers with yellow green-colored venation and centers.
6. Resistance to mildew.
7. Good garden performance.

Plants of the new *Petunia* can be compared to plants of the parent selections. Plants of the new *Petunia* differ primarily from plants of the parent selections in plant uniformity, flowering habit and flower color.

Plants of the new *Petunia* can also be compared to plants of the *Petunia* 'Kerveryello', not patented. In side-by-side comparisons conducted in Dresden, Germany, plants of the new *Petunia* and 'Kerveryello' differed primarily in the following characteristics:

1. Plants of the new *Petunia* were more freely branching than plants of 'Kerveryello'.
2. Plants of the new *Petunia* flowered earlier than plants of 'Kerveryello'.
3. Plants of the new *Petunia* had slightly smaller flowers than plants of 'Kerveryello'.
4. Plants of the new *Petunia* and 'Kerveryello' differed slightly in flower color.
5. Plants of the new *Petunia* were resistant to mildew whereas plants of 'Kerveryello' were susceptible to mildew.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet comprises a side perspective view of a typical flowering plant of 'Sutulim'.

The photograph on the second sheet is a close-up view of typical flowers of 'Sutulim'.

DETAILED BOTANICAL DESCRIPTION

The aforementioned photographs and following observations, measurements and values describe plants grown during the spring in 13-cm containers in a glass-covered greenhouse in Dresden, Germany and under cultural practices typical of commercial production. During the production of the plants, day temperatures averaged 18° C., night temperatures averaged 16° C. and light levels ranged from 15 to 90 klux. Plants were pinched two times and were four months old when the photographs and description were taken. In the following description, color references are made to The Royal Horticultural Society Colour Chart, 1995 Edition, except where general terms of ordinary dictionary significance are used.

Botanical classification: *Petunia×hybrida* 'Sutulim'.

Parentage:

*Female, or seed, parent*.—Unnamed proprietary selection of *Petunia×hybrida*, not patented.

*Male, or pollen, parent*.—Unnamed proprietary selection of *Petunia×hybrida*, not patented.

Propagation:

*Type*.—By terminal cuttings.

*Time to initiate roots, summer*.—About seven days at temperatures about 18° C. to 20° C.

*Time to initiate roots, winter*.—About seven to nine days at temperatures about 18° C. to 20° C.

*Time to produce a rooted young plant, summer*.—About three weeks at temperatures about 18° C. to 20° C.

*Time to produce a rooted young plant, winter*.—About three to four weeks at temperatures about 18° C. to 20° C.

*Root description*.—Fibrous; medium in thickness.

*Rooting habit*.—Freely branching, dense.

Plant description:

*Plant and growth habit*.—Upright and mounding plant habit; freely branching habit with about eight to ten lateral branches developing per plant; pinching enhances lateral branch development; moderately vigorous growth habit and rapid growth rate.

*Plant height*.—About 30 cm to 33 cm.

*Plant diameter*.—About 35 cm to 37 cm.

Lateral branch description:

*Length*.—About 16 cm to 22 cm.

*Diameter*.—About 3 mm to 4 mm.

*Internode length*.—About 1 cm to 2 cm.

*Strength*.—Moderately strong, flexible.

*Aspect*.—Upright to outwardly spreading.

*Texture*.—Pubescent; viscid.

*Color*.—Close to 144A.

Leaf description:

*Arrangement*.—Alternate and opposite, simple.

*Length*.—About 2 cm to 6 cm.

*Width*.—About 1 cm to 3.5 cm.

*Shape*.—Ovate.

*Apex*.—Acute or obtuse.

*Base*.—Attenuate.

*Margin*.—Entire.

*Texture, upper and lower surfaces*.—Pubescent, viscid.

*Venation pattern*.—Pinnate; reticulate.

*Color*.—Developing leaves, upper surface: Close to 146A. Developing leaves, lower surface: Close to 146B. Fully expanding leaves, upper surface: Close to 147A; venation, close to 146C. Fully expanding leaves, lower surface: Close to 147B; venation, close to 146C.

*Petioles*.—Length: About 5 mm to 10 mm. Diameter: About 2 mm. Texture, upper and lower surfaces: Pubescent, viscid. Color, upper and lower surfaces: Close to 146C.

Flower description:

*Flower arrangement and habit*.—Single salverform flowers arising from upper leaf axils; freely flowering habit; flowers face upright to outwardly.

*Fragrance*.—None detected.

*Natural flowering season*.—Early flowering habit, plants of the new Petunia begin flowering about five to six weeks after planting; long flowering period; flowering commences naturally during the spring and plants flower continuously throughout the summer and autumn until frost in Germany.

*Flower longevity*.—Individual flowers last about five to six days on the plant; flowers persistent.

*Flower buds*.—Length: About 3 cm to 4 cm. Diameter: About 5 mm to 10 mm. Shape: Tubular. Color: Close to 144C.

*Flower diameter*.—About 5 cm to 5.5 cm.

*Flower length (depth)*.—About 4 cm to 4.5 cm.

*Tube length*.—About 2.5 cm to 3 cm.

*Corolla*.—Arrangement: Five petals fused at the base and opening into a flared trumpet. Petal length from throat: About 2.5 cm. Petal width: About 2.5 cm to 3 cm. Petal shape: Roughly spatulate, rounded. Petal apex: Rounded. Petal margin: Slightly serrate; undulate. Petal texture, upper and lower surfaces: Smooth, glabrous. Throat texture: Smooth, glabrous. Tube texture: Smooth, glabrous. Color: Petal, when opening, upper surface: Close to 157C; towards the center, close to 151C. Petal, when opening, lower surface: Close to 157C, towards the center, close to 145C. Petal, fully opened, upper surface: Close to 157B; towards the center, close to 151D; venation, close to 151D. Petal, fully opened, lower surface: Close to 157B; towards the center, close to 145C; venation, close to 145C. Throat: Close to 151D; venation, close to 151D. Tube: Close to 145C; venation, close to 145C.

*Calyx*.—Arrangement: One star-shaped calyx with five sepals fused at the base per flower. Sepal length: About 1 cm to 3 cm. Sepal width: About 1 mm to 5 mm. Sepal shape: Oblong. Sepal apex: Obtuse, slightly acute. Sepal margin: Entire. Sepal texture, upper and lower surfaces: Pubescent; viscid. Color, upper surface: Close to 146A. Color, lower surface: Close to 146B.

*Peduncles*.—Length: About 2.5 cm to 4.5 cm. Diameter: About 1 mm to 2 mm. Aspect: About 25° to 40° from vertical. Strength: Moderately strong. Texture: Pubescent; viscid. Color: Close to 146B.

*Reproductive organs*.—Stamens: Quantity and arrangement: Five per flower. Filament length: About 2 cm to 2.5 cm. Filament color: Close to 155D. Anther shape: Reniform. Anther length: About 1 mm to 2 mm. Anther color: Close to 2D. Pollen amount: Abundant. Pollen color: Close to 2D. Pistils:

Quantity: One per flower. Style length: About 2 cm to 2.5 cm. Style color: Close to 146C. Stigma shape: Rounded, parted. Stigma color: Close to 146B. Ovary color: Close to 144B. Seeds and fruits: Seed and fruit development have not been observed on plants of the new *Petunia*.

Garden performance: Plants of the new *Petunia* have been observed to have good garden performance and to tolerate rain, wind and temperatures ranging from about 1° C. to about 35° C. to 40° C.

Pathogen & pest resistance: Plants of the new *Petunia* have been observed to be resistant to mildew (*Podosphaera xanthii*). Plants of the new *Petunia* have not been observed to be resistant to pests and other pathogens common to *Petunia* plants.

It is claimed:

1. A new and distinct *Petunia* plant named 'Sutulim' as illustrated and described.

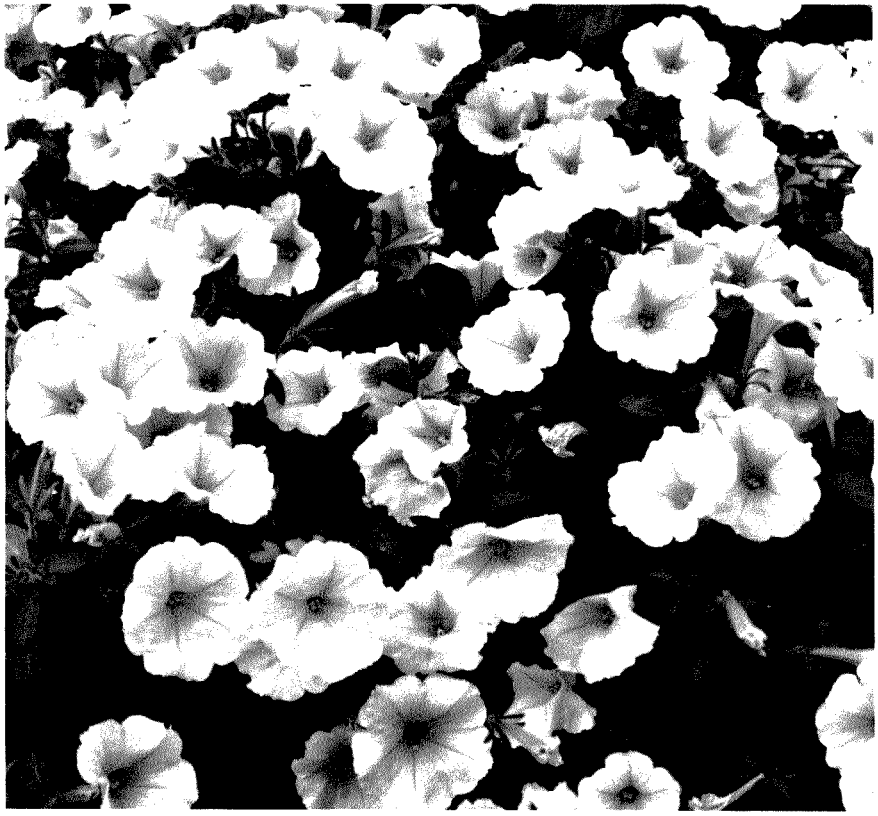

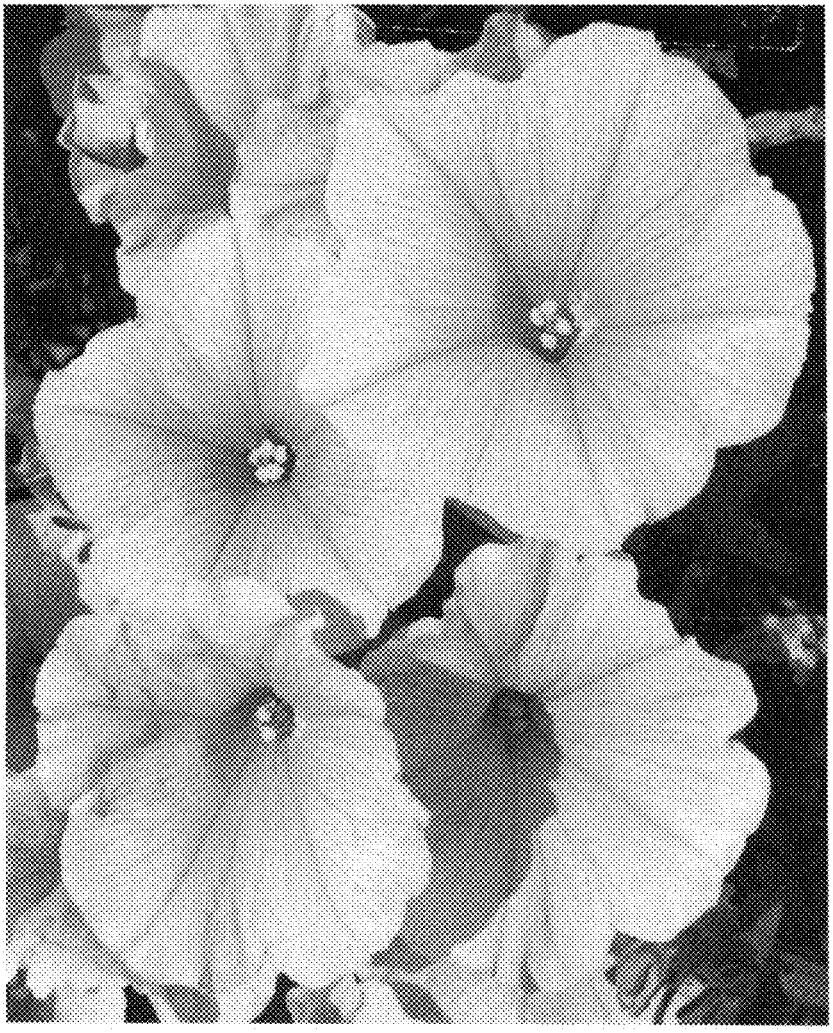

* * * * *